(12) United States Patent
Kraemer et al.

(10) Patent No.: US 7,364,103 B2
(45) Date of Patent: Apr. 29, 2008

(54) METHOD AND DEVICE FOR THE ALIGNMENT AND LOCATION OF A SAMPLE SUCH AS TABLETS, PILLS OR TABLETTES

(75) Inventors: Norbert Kraemer, deceased, late of Darmstadt (DE); Thilo Kraemer, legal representative, Darmstadt (DE)

(73) Assignee: Kraemer Eletronik GmbH, Darmstadt (DE)

( * ) Notice: Subject to any disclaimer, the term of this patent is extended or adjusted under 35 U.S.C. 154(b) by 299 days.

(21) Appl. No.: 10/531,559

(22) PCT Filed: May 20, 2001

(86) PCT No.: PCT/DE01/01903

§ 371 (c)(1),
(2), (4) Date: Dec. 5, 2005

(87) PCT Pub. No.: WO01/90743

PCT Pub. Date: Nov. 29, 2001

(65) Prior Publication Data

US 2006/0260413 A1    Nov. 23, 2006

(30) Foreign Application Priority Data

May 22, 2000 (DE) ................. 100 24 970

(51) Int. Cl.
*B02C 1/00* (2006.01)
*B65G 47/14* (2006.01)
(52) U.S. Cl. .............. 241/262; 241/198.1; 241/199.11; 241/205; 241/264; 198/752.1; 198/766; 73/818
(58) Field of Classification Search ............... 73/818; 198/752.1, 766; 241/198.1, 199.11, 205, 241/262–266
See application file for complete search history.

(56) References Cited

U.S. PATENT DOCUMENTS 4,236,413 A    12/1980  Schmid et al.

(Continued)

FOREIGN PATENT DOCUMENTS

DE    3541672    11/1985

(Continued)

*Primary Examiner*—Edward Lefkowitz
*Assistant Examiner*—Jonathan Dunlap
(74) *Attorney, Agent, or Firm*—Horst H. Kasper

(57) ABSTRACT

The invention relates to a device for the alignment and location of a sample (7), such as pills or tablets, for carrying out a further method step, such as a hardness test, with the aid of two opposing jaws (2, 3, 21), which may be moved relative to each other, the movable compression jaw (2) of which displaces the sample (7) along a guide track on to the fixed counter-jaw (3, 21), in order to begin the further method step with the sample (7). The forward movement of the movable compressing jaw (2), along with the sample (7) towards the fixed counter-jaw (3, 21) is continuously interrupted, the compressing jaw (2) being drawn backwards and driven forwards, such that the sample oscillates about the rest position thereof and then the compressing jaw (2) continues the movement towards the counter-jaw (3, 21) until the sample (7) reaches said counter-jaw (21). Furthermore, the fixed jaw (3, 21) and/or the guide track (6, 34) may be set in vibration during the forward motion of the movable jaw (2) towards the fixed counter-jaw (3, 21).

12 Claims, 4 Drawing Sheets

U.S. PATENT DOCUMENTS

Figure 1:
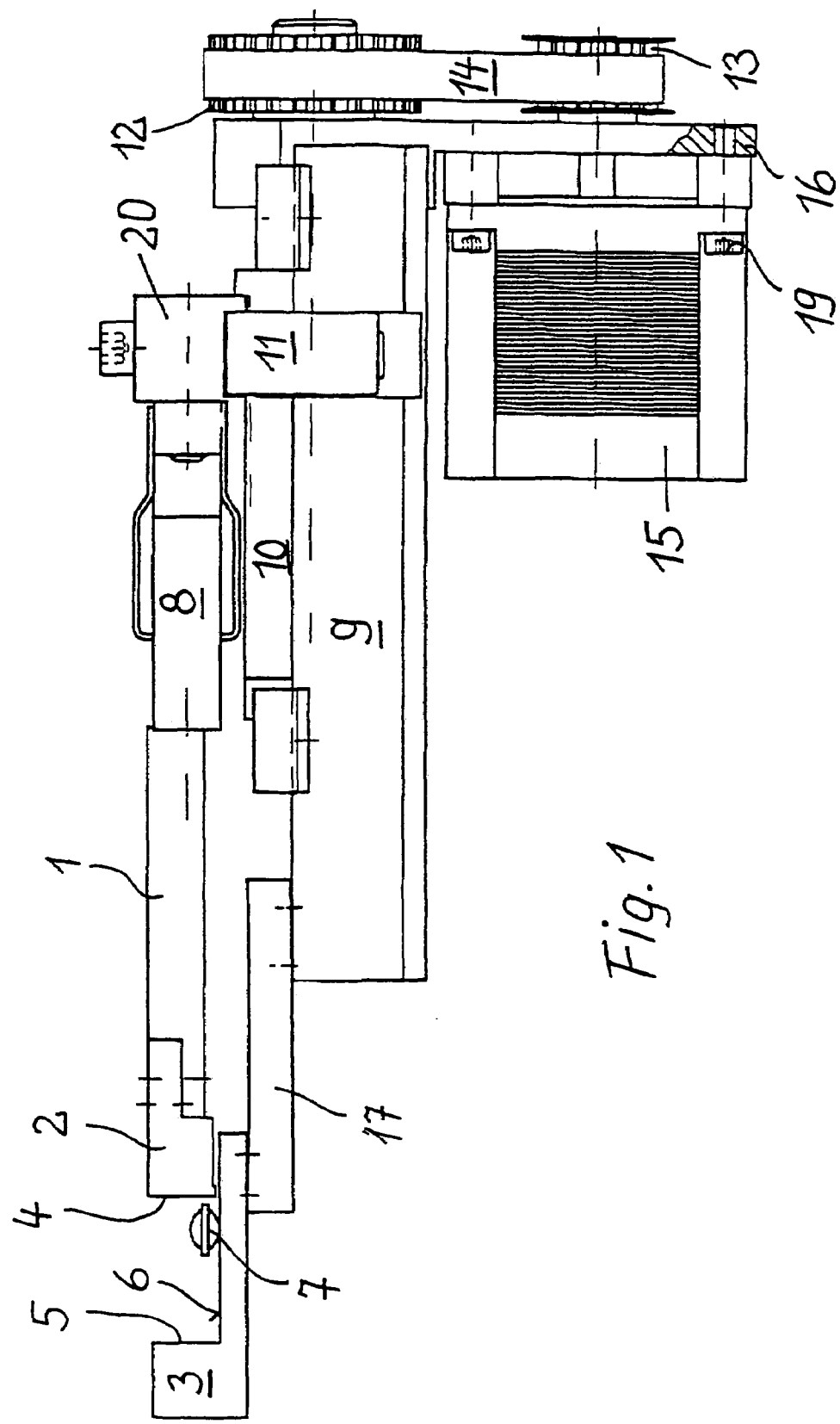

| | | | |
|---|---|---|---|
| 4,393,717 A | 7/1983 | Mason et al. | |
| 4,509,699 A * | 4/1985 | Tanaka et al. | 241/268 |
| 4,660,713 A * | 4/1987 | Kaminski | 198/443 |
| 5,140,861 A | 8/1992 | Gleason et al. | |
| 5,555,768 A | 9/1996 | Shaffer et al. | |
| 6,155,507 A * | 12/2000 | Ostergaard | 241/264 |
| 6,237,743 B1 * | 5/2001 | Bracher | 198/464.2 |
| 6,257,079 B1 * | 7/2001 | Mueller | 73/866 |
| 6,260,419 B1 * | 7/2001 | Kramer | 73/821 |
| 6,711,962 B1 * | 3/2004 | Gerteis | 73/866 |
| 6,820,498 B2 * | 11/2004 | Kalbermatten | 73/856 |

FOREIGN PATENT DOCUMENTS

| | | |
|---|---|---|
| DE | 19516643 | 5/1995 |
| DE | 19554612 | 12/1996 |
| DE | 19744227 | 10/1997 |
| WO | 8503278 | 1/1985 |
| WO | 9819945 | 5/1998 |

* cited by examiner

METHOD AND DEVICE FOR THE ALIGNMENT AND LOCATION OF A SAMPLE SUCH AS TABLETS, PILLS OR TABLETTES

TECHNICAL AREA

The invention relates to a method for aligning and moving a test specimen such as, for instance, tablets, pills, lozenges or tabs, which are cambered or rounded on at least one of their main surfaces and are thus able to execute rocking oscillations starting from a resting position, in order to carry out another process step such as a hardness test, involving the test specimen, making use of two jaws arranged opposite from each other and movably relative to each other, whereby the movable pressing jaw pushes the test specimen forward on a guide segment towards the stationary counter-jaw until the test specimen makes mechanical contact with the counter-jaw, so as to initiate the further process step involving the test specimen, according to the generic part of claim 1. The invention likewise relates to a device for performing the method, according to the generic part of claim 6.

STATE OF THE ART

Within the scope of quality control in the production of tablets, pills or lozenges, but also in the production of tablets in the detergent industry, there is a need to determine the mechanical-physical properties of such articles such as, for example, their weight, dimensions, disintegration time in a medium and hardness. For this purpose, tablet testing systems are known that examine several tablets from a production cycle in terms of these properties. Tablets from a batch are removed from a storage container one at a time and conveyed, for example, by means of a transport star or a conveyor belt from one measurement station to the next. As a rule, the periphery of such a transport star has 24 chambers that each serve to receive a tablet test specimen one at a time. First of all, a weighing procedure is carried out; this is followed by a measuring device for determining the dimensions of the test specimen, and then followed by a hardness tester. The interaction of the individual stations as well as the storage and transmission of the measured results are implemented by software and by a central computer unit.

The hardness of a test specimen is normally measured in a fine-resolution load cell that has a pressure piston and a counter bearing, namely, a stationary counter-jaw and a movable pressing jaw. The test specimen is conveyed in the area between the counter-jaw and the movable pressing jaw on a guide segment, whereby the test specimen is preferably in contact with the counter-jaw. The pressing jaw is now moved by means of a stepping motor against the counter-jaw and against the test specimen lying in front of said counter-jaw. The force being exerted by the pressing jaw with each step of the motor is measured and recorded, said force being constant and very small, as long as the counter-jaw is not touching the tablet or when it is just pushing it over the guide segment without the counter-pressure of the counter-jaw. Once the pressing jaw presses the test specimen against the counter-jaw, the force exerted by the pressing jaw increases with each step of the stepping motor until the test specimen breaks apart. The force employed to break it apart is recorded and this serves as a measure of the hardness of the test specimen. The abrupt drop in the force employed by the pressing jaw in breaking apart the test specimen serves as a termination condition for ending the measurement. The pressing jaw is retracted to its starting position and the next test specimen can be tested.

WO 98/53298 describes such a device for performing hardness tests, which comprises a testing table for receiving the test specimen as well as a pressure piston that can be moved linearly and a counter-bearing, which are arranged above the testing table and which can be moved towards each other. The test specimen is located between the pressure piston and the counter-bearing, whereby the force employed in pressing the pressure piston and the counter-bearing against each other or a parameter that is proportional to said force can be measured by means of a force-measuring device and the hardness of the test specimen is determined on this basis. However, test specimens that have at least one cambered or rounded main surface, for example, that have a lens-shaped design, tilt when they are pushed by means of the pressing jaw and, while they are being pushed further forward, they end up between the pressing jaw and the counter-jaw in such a tilted position that, when the test specimen is in this tilted state, no informative hardness test can be carried out; it could even happen that the test specimen might become positioned upright between the jaws. However, in order to determine the diameter of a test specimen and in order to carry out a hardness test, a test specimen has to lie horizontally on the guide segment, because only the force measured in this position is informative in a hardness test and is approved, for example, in the pharmaceutical sector.

DE 196 54 612 C2 describes a method and a device for checking tablet parameters, which has a vibrator that serves to place the tablet in a defined and stable position with respect to its center of gravity so that the tablet height can be measured. This is supposed to ensure that the height and thickness of the tablet—irrespective of its shape—can be measured by means of the known methods. The vibrator consists of two horizontally arranged and coupled plates, whereby the tablet is positioned on the upper plate in order to carry out the measurements while the lower plate executes the vibrating motions, which are then transmitted to the upper plate.

U.S. Pat. No. 4,393,717 describes a tablet testing device which, for purposes of transporting the tablets, has a V-shaped and inclined trough that is coupled to a vibrator in order to transport the tablets through the trough one at a time.

DE 35 41 672 A1 describes a device on packaging machines for purposes of an orderly feed and placement of small parts that are to be packaged such as, for example, tablets, tabs and lozenges, said device having two pushing elements that are movable with respect to each other and that cross paths. The pushing elements are at times made to vibrate in order to facilitate the alignment and placement of the small parts in correspondingly shaped recesses in the pushing elements. The lower of the two pushing elements can execute an advancing movement in order to put the small parts into fitting positions for purposes of packaging them.

TECHNICAL OBJECTIVE

The invention is based on the objective of creating a method and a device of the above-mentioned type with which it is also possible to measure the diameter of a test specimen that has at least one cambered or rounded main surface, for example, that has a lens-shaped design, and to perform a hardness test on the test specimen and to push the test specimen or to push it over, a process in which tilting of the test specimen should be ruled out.

DISCLOSURE OF THE INVENTION AS WELL AS OF ITS ADVANTAGES

The achievement of the objective of the method according to the invention consists in the fact that, while carrying along the test specimen, the advancing movement of the movable pressing jaw in the direction of the stationary counter-jaw is continuously interrupted, and the pressing jaw retreats and advances, whereby the advancing and retreating movement of the pressing jaw is small relative to its total advancing distance with respect to the counter-jaw, but all in all, the pressing jaw moves towards the counter-jaw while each time carrying along the test specimen by the small advancing distance and releasing the test specimen by retreating, so that the test specimen oscillates back into its resting position and then the pressing jaw starts up again to push in the direction of the counter-jaw until the test specimen has reached the counter-jaw, or else the stationary counter-jaw and/or the guide segment are made to oscillate during the advancing movement of the movable pressing jaw in the direction of the stationary counter-jaw, said oscillations acting on the test specimen so that, during the advancing movement of the pressing jaw, the test specimen executes a rocking and/or vibrating oscillation that continuously causes the test specimen to oscillate back into the resting position or allows it to oscillate around said resting position until the test specimen has reached the counter-jaw and the oscillation of the test specimen is stopped by the stationary counter-jaw. This forward and backward movement of the movable pressing jaw in the direction of the stationary counter-jaw is carried out until the test specimen is just touching the stationary counter-jaw. Now, first of all, the diameter of the test specimen can be determined and subsequently, for example, the hardness test can be carried out and the test specimen can be broken apart.

The method according to the invention has the outstanding advantage that now, the measurement of the diameter as well as the performance of a hardness test are possible with a test specimen that has at least one cambered or rounded main surface, for example, that has a lens-shaped design. The working method ensures that the test specimen lies horizontal, at the latest when it comes to lie against the counter-jaw, for purposes of determining the diameter or performing the hardness test; tilting is ruled out, at least at this point in time. As a matter of principle, the horizontal alignment of the test specimen can be achieved by moving the pressing jaw back and forth or else by vibrating the counter-jaw and/or the guide segment.

In another advantageous embodiment of the invention, the movable pressing jaw pushes the test specimen along in front of it while, if applicable, tilting the test specimen until the latter reaches the stationary counter-jaw, after which the movable pressing jaw retreats until the test specimen has oscillated into its resting position, and subsequently the pressing jaw moves once again in the direction of the stationary counter-jaw in order to initiate the hardness test.

Moreover, the docking of the test specimen at the stationary counter-jaw can be monitored by means of a video camera that emits a signal at the time of the docking which serves to control the electric motor that drives the movable pressing jaw. In another embodiment of the method, during its advancing movement in the direction of the stationary counter-jaw, the movable pressing jaw executes vibrations in the direction of its longitudinal axis back and forth relative to the counter-jaw, said vibrations being superimposed upon the advancing movement of the pressing jaw.

A device of the type described above for performing the method consists in the fact that the pressing jaw, with a continuous interruption of its advancing movement, can be moved back and forth along small advancing and retreating distances relative to its total advancing distance with respect to the counter-jaw, but all in all, it is able to move towards the counter-jaw while carrying along the test specimen by the small advancing distance and releasing the test specimen by retreating, until the test specimen has reached the counter-jaw, or else the stationary jaw and/or the guide segment can be made to oscillate around a resting position during the advancing movement of the movable pressing jaw in the direction of the stationary jaw by means of an oscillation generator, said oscillations acting on the test specimen so that, during the advancing movement of the test specimen, it is also able to execute a rocking and/or vibrating oscillation. Thus, as a matter of principle, both embodiments are possible, namely, that the pressing jaw moves back and forth, but in the sense of a backwards and forward movement that is superimposed upon the advancing movement of the pressing jaw, or else the counter-jaw and/or the guide segment vibrate.

The movable pressing jaw as well as a load cell attached to it to create a hardness tester are arranged on a carriage that can be moved on a stationary guide rail and that can be moved back and forth by means of an electric stepping motor as well as by a drive gear by small advancing and retreating distances relative to its total advancing distance with respect to the counter-jaw.

Above the stationary counter-jaw, there is a video camera for monitoring the docking of the test specimen at the stationary counter-jaw, said camera generating an electric signal that serves to influence the electric motor.

The method and the device for aligning and moving a test specimen such as, for instance, tablets, pills, lozenges or tabs, which are cambered or rounded on at least one of their main surfaces and are thus able to execute rocking oscillations starting from a resting position, in order to carry out another process step such as a hardness test or a pushing over procedure, involving the test specimen, having a movable pushing jaw for moving the test specimen on a guide segment so as to initiate the further process step involving the test specimen, can also be used separately from a hardness testing procedure and can be configured for this purpose, for example, if a test specimen with such a shape is to be pushed over horizontally. In this case, there is a pushing jaw that, with a continuous interruption of its advancing movement, can be moved back and forth along small advancing and retreating distances relative to its total advancing distance, but all in all, while each time carrying along the test specimen on the guide segment by the small advancing distance and releasing the test specimen by retreating, can be moved until the test specimen has reached the desired place. Or else the guide segment can be made to oscillate around a resting position during the advancing movement of the movable pushing jaw by means of an oscillation generator, said oscillations acting on the test specimen so that the test specimen is also able to execute a rocking and/or vibrating oscillation during the advancing movement of the movable pressing jaw and the jiggling movement of the test specimen is only stopped by the stationary counter-jaw.

BRIEF DESIGNATION OF THE DRAWING IN WHICH THE FOLLOWING IS SHOWN

Figure 2:
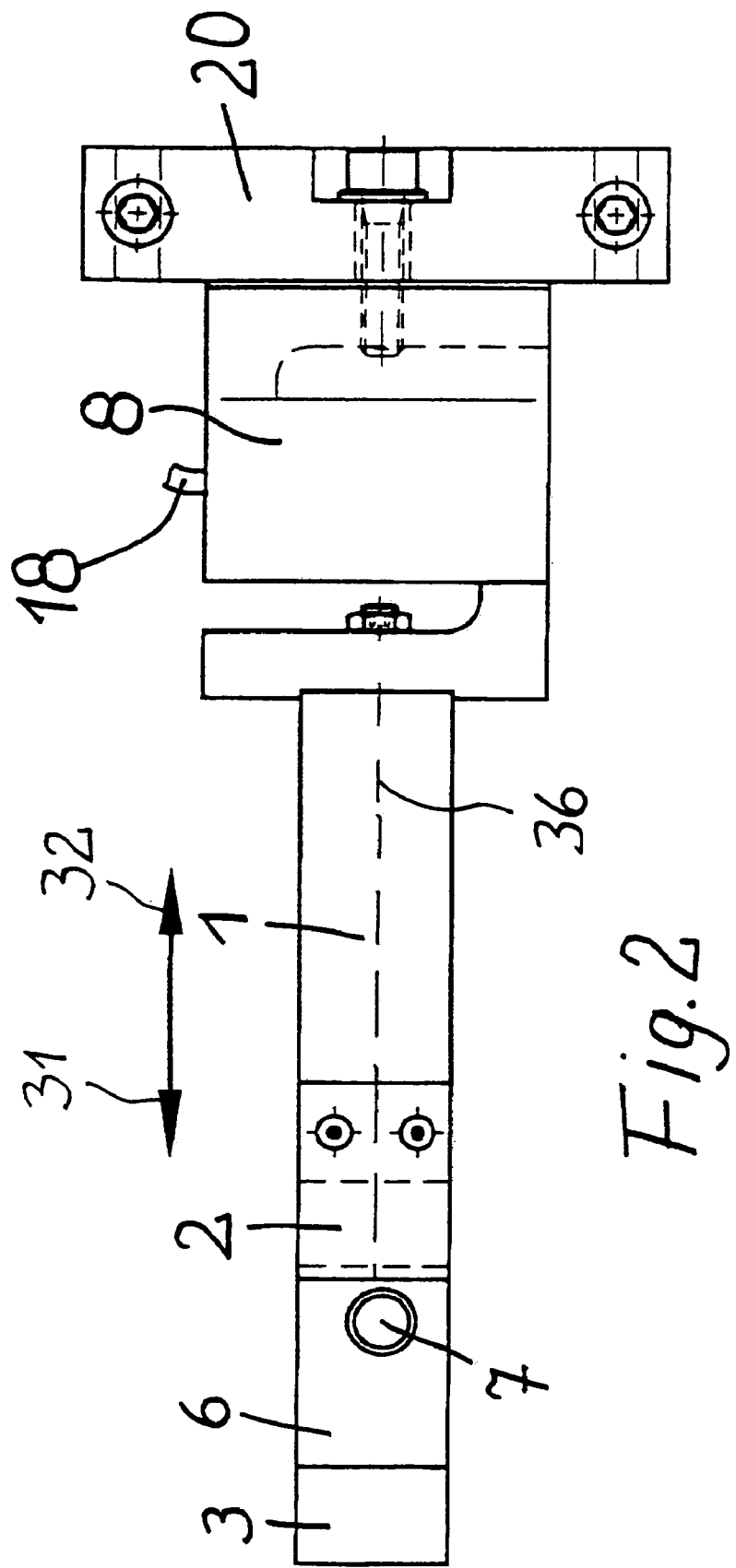
Figure 3:
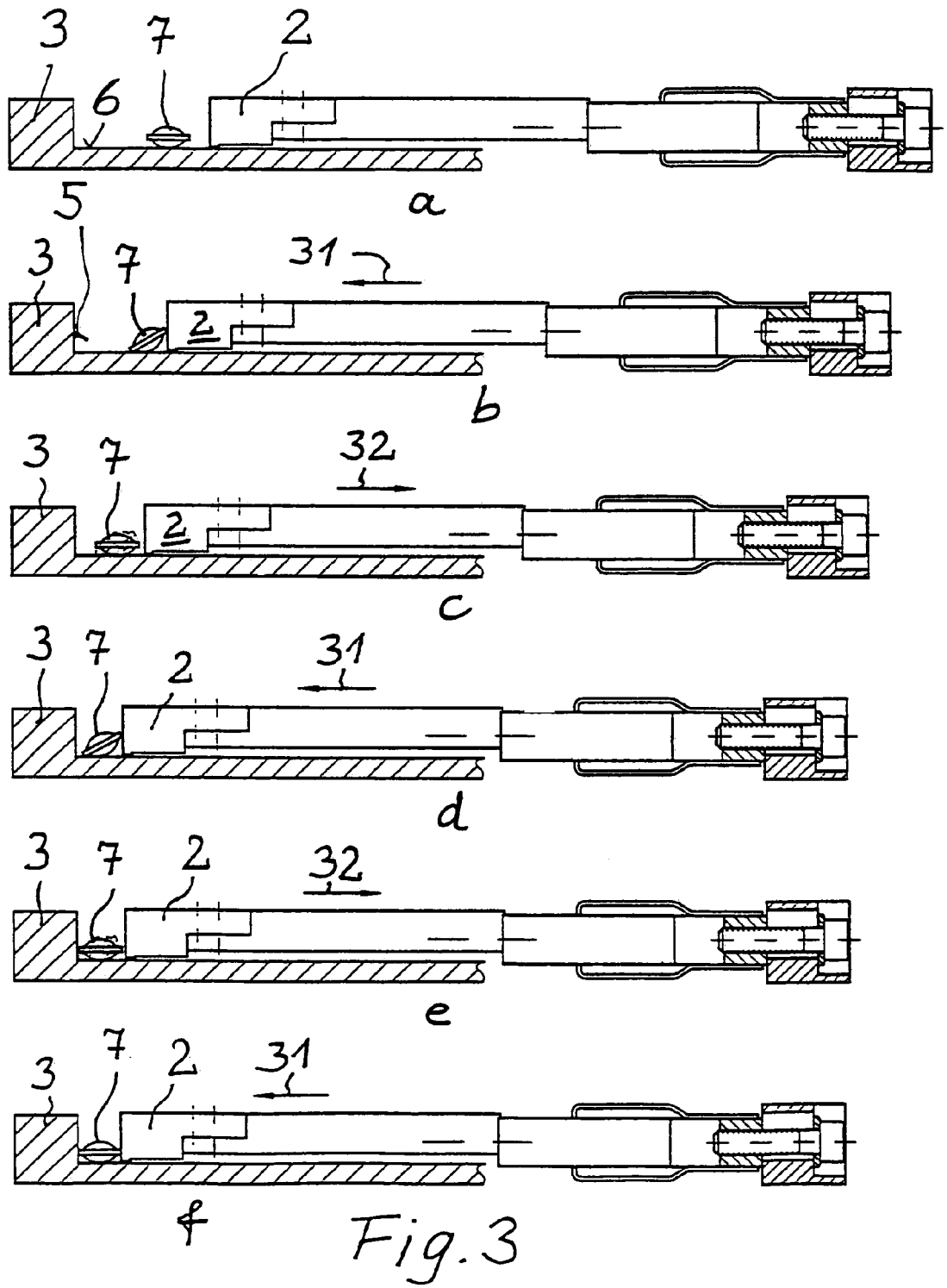
Figure 4:
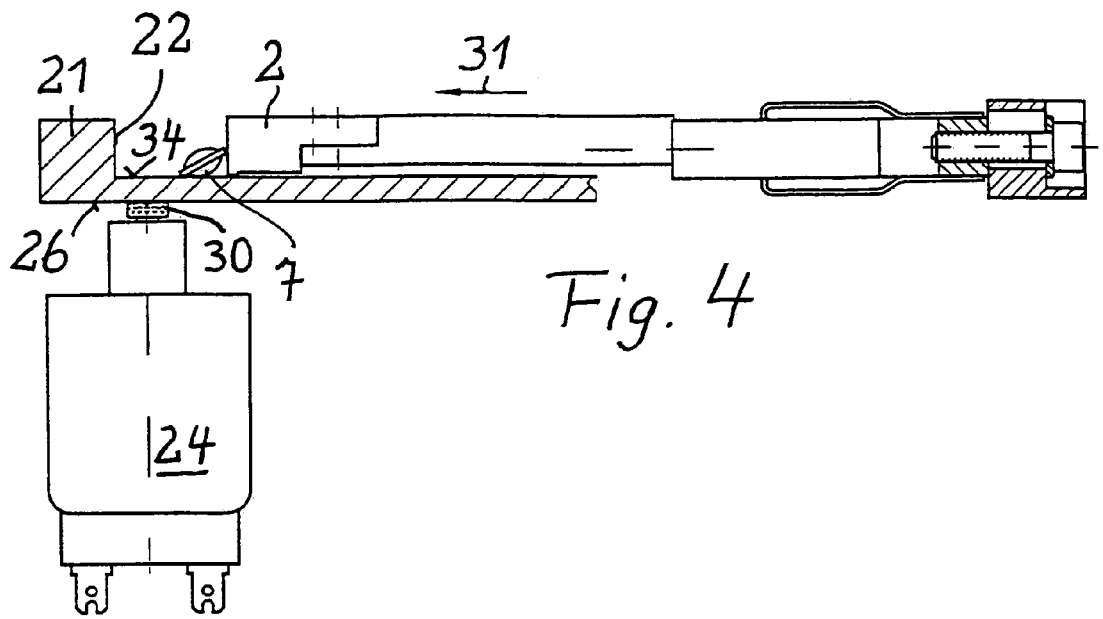
Figure 5:
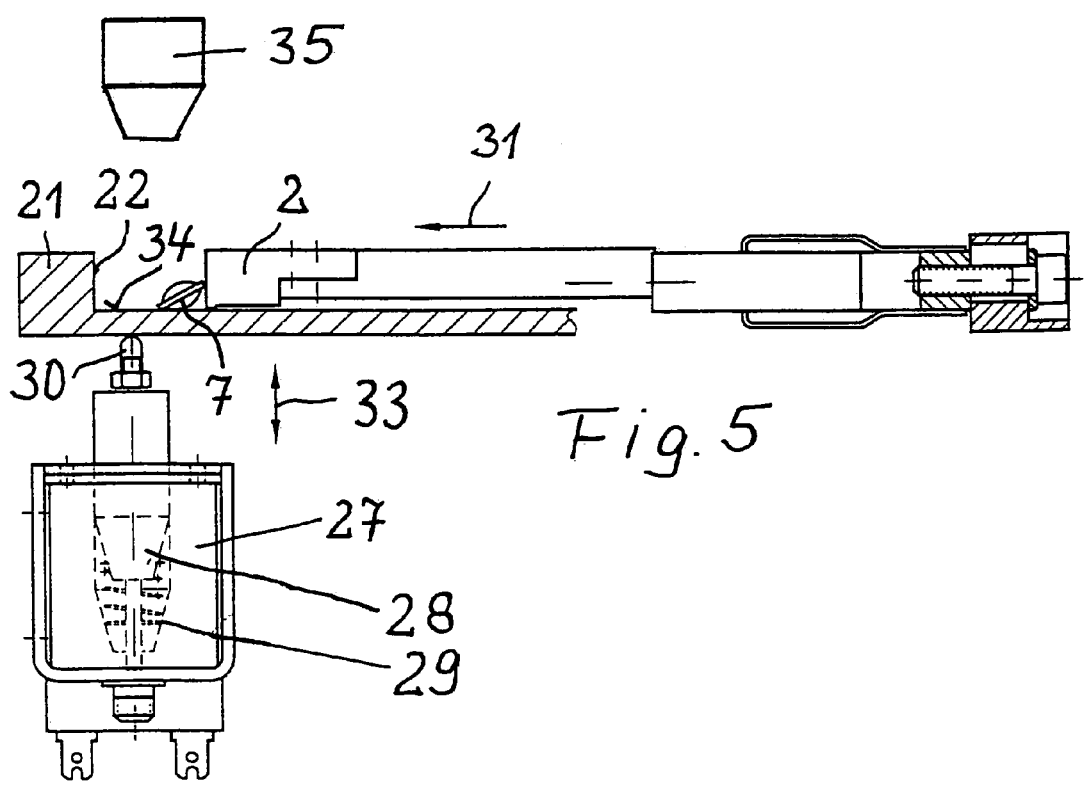

FIG. 1 a schematic general view of a hardness test device
FIG. 2 a top view of FIG. 1
FIG. 3a-f the movement of the movable pressing jaw relative to the stationary counter-jaw
FIGS. 4 and 5 each a view of a hardness testing device with a vibrator that causes the vibration of the counter-jaw and/or the guide segment on which the test specimen is located.

PREFERRED EMBODIMENT OF THE INVENTION

According to FIGS. 1 and 2, by way of an example, a hardness testing device for test specimens such as tablets, pills, lozenges or tabs is shown, consisting of a plunger 1 that has a pressing jaw 2 on its front end and that has a vertically upright pushing surface 4. The back end of the plunger is connected to a load cell 8 that has an electric connection line 18, whereby the load cell 8 according to FIG. 2 is attached to a crossbeam 20. The plunger 1, together with the load cell 8, is mounted on a carriage 10 that can be moved on a stationary guide rail 9 lengthwise in the direction of the longitudinal axis 36 of the plunger 1. The front section of the guide rail 9 also has a holding part 17 to which a guide segment 6 and a counter-jaw 3 with a vertical face wall 5 are attached. Thus, the counter-jaw 3, the guide segment 6, the holding part 17 and the guide rail 9 are at rest relative to the carriage 10 and thus to the plunger 1.

An electric motor 15, which is preferably a stepping motor, is attached to the guide rail 9 in a suitable manner by means of a plate 16 and screws 19 and, via a toothed wheel 13 and a toothed belt 14, said motor drives another toothed wheel 12. This toothed wheel 12 is connected via a carrier 11 to the carriage 10 or to the crossbeam 20; via the carrier 11, the carriage 10 is moved forward or backward on the guide rail 9 when the toothed wheel gear rotates forward or backward. In this manner, the pressing jaw 2 moves over the guide rail 6 towards or away from the counter-jaw 3.

FIG. 3a-f shows a lens-shaped test specimen 7 on the guide segment 6 between the stationary counter-jaw 3 and the movable pressing jaw 2; the test specimen 7 in FIG. 3a lies horizontal in its resting position. Now, according to FIG. 3a, the pressing jaw 2 moves in the direction indicated by the movement arrow 31 towards the counter-jaw 3, carries the test specimen 7 along and tilts it. Then the pressing jaw 2 moves according to FIG. 3c in the direction indicated by the movement arrow 32 back by a short path so that the test specimen 7 can oscillate back into its resting position. Now the pressing jaw 2 moves once again in the direction of the indicated by the movement arrow 31 according to FIG. 3d up to the test specimen, pushes and tilts it again, whereby the pressing jaw 2 moves close to the opposite counter-jaw 3. According to FIG. 3e, the pressing jaw moves back again by a short path length so that the test specimen 7 can oscillate back into its resting position again and either already touches or almost touches the face wall 5 of the counter-jaw 3. The short path length by which the pressing jaw 2 has to retract so that the test specimen 7 can assume its resting position again is defined by the cosine of the positioning angle of the test specimen 7. As soon as the test specimen has assumed its horizontal position shown in FIG. 3e, the pressing jaw 2 according to FIG. 3f once again advances towards the counter-jaw 3 in the direction indicated by the movement arrow 31, whereby the diameter of the test specimen 7 (as a function of the pressure increase) is measured merely by clamping the test specimen between the jaws. When the pressing jaw 2 advances further toward the counter-jaw 3, the hardness test of the test specimen 7 is initiated until said test specimen breaks apart.

Thus, while carrying along the test specimen 7, the advancing movement of the movable pressing jaw 2 in the direction of the stationary counter-jaw 3 is continuously interrupted and the pressing jaw 2 retreats and advances, whereby the advancing and retreating movement of the pressing jaw 2 is small relative to its total advancing distance with respect to the counter-jaw 3; but all in all, the pressing jaw 2 moves towards the counter-jaw 3 while each time carrying along the test specimen 7 by the small advancing distance and, each time, releasing the test specimen by retreating, so that the test specimen oscillates back into its resting position and then the pressing jaw 2 starts up again to push in the direction of the counter-jaw 3, 21 until the test specimen 7 has reached the counter-jaw 21. This forward and backward movement of the movable pressing jaw 2 in the direction of the stationary counter-jaw 3 is carried out until the test specimen 7 is just touching the stationary counter-jaw 3.

FIGS. 4 and 5 show two embodiments in which the pressing jaw, while it is advancing, does not execute any superimposed backward and forward movements relative to the horizontal alignment of the test specimen 7. On the contrary, the stationary jaw 21 and/or the guide segment 34 are made to oscillate during the advancing movement of the movable pressing jaw 2 in the direction of the stationary counter-jaw 21 by means of a vibrator 24, 27 or other vibrating mechanism, said oscillations acting on the test specimen 7 so that, during the advancing movement of the pressing jaw 2, the test specimen is, in fact, tilted at the beginning at the moment when the advancing movement starts, but it also executes a rocking and/or vibrating oscillation or jiggling movement that continuously causes the test specimen 7 to oscillate back into its resting position or allows it to oscillate around said resting position until the test specimen 7 has reached the counter-jaw 21 and the oscillation of the test specimen 7 is stopped by the stationary counter-jaw 21.

The vibrators 24, 27 each have a plunger 30 that engages below the guide segment 34 close to the counter-jaw 21 and it transmits its oscillations to the counter-jaw 21 and/or to the guide segment 34. As a result, the test specimen 7 makes a jiggling movement until it reaches the vertical face wall 22 of the counter-jaw.

The vibrator shown in FIG. 5 is an electromagnetic vibrator 27 that has an electromagnet 28 for purposes of generating the vibration, which is restored by means of a return spring 29. Above the jaws 2, 21 and especially in the area of the counter-jaw 21, there can be a video camera 35 for visually monitoring the docking or approach of the test specimen 7 to the counter-jaw. An acquired optical signal is converted into an output signal which can be used for driving and influencing the electric motor 15 (FIG. 1).

INDUSTRIAL APPLICABILITY

The invention is especially suitable for use in tablet testing stations where lens-shaped or cambered or oval tablets or pills or lozenges or tabs are to be measured and tested in terms of various tablet or tab parameters such as hardness, height or diameter and others. The special usefulness of the method lies in the fact that now the measurement of the diameter as well as well as the performance of a hardness test are possible with a test specimen that has at least one cambered or rounded main surface, for example, that has a lens-shaped design. The working method ensures that the test specimen lies horizontal, at the latest when it comes to lie against the counter-jaw for purposes of determining the diameter or performing the hardness test; tilting is ruled out, at least at this point in time.

LIST OF REFERENCE NUMERALS 1, 25, 30 plunger
2 movable jaw or pressing jaw
3, 21 stationary jaw or counter-jaw
4 pushing surface
5, 22 face wall of the jaws 2, 3, 22
6, 34 straight guide segment of the jaw 3, 21 for the test specimen
7, 23 lens-shaped tablet or lozenge
8 load cell
9 guide rail
10 carriage
11 carrier
12,13 toothed wheels
14 toothed belt
15 electric motor (stepping motor)
16 plate
17 holding part
18 electric connection of the load cell
19 screws
20 crossbeam
24, 27 vibrator
26 engagement surface below the straight surface 6, 31, 34 of the jaw
28 electromagnet
29 return spring
31, 32, 33 movement arrows
35 video camera
36 longitudinal axis of the plunger

The invention claimed is:

1. A method for aligning and moving a test specimen (7) such as, for instance, tablets, pills, lozenges or tabs, which are cambered or rounded an at least one of their main surfaces and are thus able to execute rocking oscillations starting from a resting position, in order to carry out another process step such as a hardness test, involving the test specimen (7), making use of two jaws (2, 3, 21) arranged opposite from each other and movably relative to each other, whereby the movable pressing jaw (2) pushes the test specimen (7) forward an a guide segment (6, 34) towards the stationary counter-jaw (3, 21) until the test specimen (7) makes mechanical contact with the counter-jaw (3, 21), so as to initiate the further process step involving the test specimen (7), characterized in that, while carrying along the test specimen (7), the advancing movement of the movable pressing jaw (2) in the direction of the stationary counter-jaw (3, 21) is continuously interrupted and the pressing jaw (2) retreats and advances, whereby the advancing and retreating movement of the pressing jaw (2) is small relative to its total advancing distance with respect to the counter jaw (3, 21), but all in all, the pressing jaw (2) moves towards the counter-jaw (3, 21) while each time carrying along the test specimen (7) by the small advancing distance and releasing the test specimen by retreating, so that the test specimen oscillates back into its resting position and then the pressing jaw (2) starts up again to push in the direction of the counter-jaw (3, 21) until the test specimen (7) has reached the counter jaw (3, 21) or the stationary jaw (3, 21) and/or the guide segment (6, 34) are made to oscillate during the advancing movement of the movable pressing jaw (2) in the direction of the stationary jaw (3, 21), said oscillations acting an the test specimen (7) so that, during the advancing movement of the pressing jaw (2), the test specimen (7) executes a rocking and/or vibrating oscillation that continuously causes the test specimen (7) to oscillate back into the resting position or allows it to oscillate around said resting position until the test specimen (7) has reached the counter-jaw (3, 21) and the oscillation of the test specimen (7) is stopped by the stationary counter-jaw (3, 21).

2. The method according to claim 1, characterized in that, the forward and backward movement of the movable pressing jaw (2) in the direction of the stationary counter jaw (3, 21) is carried out until the test specimen (7) is just touching the stationary counter-jaw (3, 21).

3. The method according to claim 1, characterized in that, the movable pressing jaw (2) pushes the test specimen (7) along in front of it while, if applicable, tilting the test specimen (7) until the latter reaches the stationary counter-jaw (3, 21), after which the movable pressing jaw (2) retreats until the test specimen (7) has oscillated into its resting position, and subsequently the pressing jaw (2) moves once again in the direction of the stationary counter-jaw (3, 21) in order to initiate the hardness test.

4. The method according to claim 1, characterized in that the docking of the test specimen (7) at the stationary counter-jaw (3, 21) is monitored by means of a video camera (35) that emits a signal at the time of the docking which serves to control the electric motor (15) that drives the movable pressing jaw (2).

5. The method according to claim 1, characterized in that, during its advancing movement in the direction of the stationary counter jaw (3, 21), the movable pressing jaw (2) executes vibrations in the direction of its longitudinal axis (36) back and forth relative to the counter jaw (3, 21), said vibrations being superimposed upon the advancing movement of the pressing jaw (2).

6. A device for aligning and moving a test specimen (7) such as, for instance, tablets, pills, lozenges or tabs, which are cambered or rounded on at least one of their main surfaces and are thus able to execute rocking oscillations starting from a resting position, in order to carry out another process step such as a hardness test, involving the test specimen (7), with two jaws (2, 3, 21) arranged opposite from each other and movably relative to each other, whereby the movable pressing jaw (2) pushes the test specimen (7) forward an a guide segment (6, 34) towards the stationary counter-jaw (3, 21) until the test specimen (7) makes mechanical contact with the counter jaw (3, 21), so as to initiate the further process step involving the test specimen (7), characterized in that, the pressing jaw (2), with a continuous interruption of its advancing movement, can be moved back and forth along small advancing and retreating distances relative to its total advancing distance with respect to the counter-jaw (3, 21), but all in all, it is able to move towards the counter jaw (3, 21) while carrying along the test specimen (7) by the small advancing distance and releasing the test specimen by retreating, until the test specimen (7) has reached the counter-jaw (3, 21) or the stationary jaw (3, 21) and/or the guide segment (6, 34) can be made to oscillate around a resting position during the advancing movement of the movable pressing jaw (2) in the direction of the stationary jaw (3,21) by means of an oscillation generator (24, 27), said oscillations acting on the test specimen (7) so that, during the advancing movement of the test specimen (7), it is able to execute a rocking and/or vibrating oscillation.

7. The device according to claim 6, characterized in that, the movable pressing jaw (2) as well as a load cell (8) attached to it to create a hardness tester are arranged on a carriage (10) that can be moved on a stationary guide rail (9) and that can be moved back and forth by means of an electric stepping motor (5) as well as by a drive gear (12, 13, 14) by small advancing and retreating distances relative to its total advancing distance with respect to the counter-jaw (3, 21).

8. The device according to claim 7, characterized in that, the drive gear is a toothed gear (12, 13) and consists of two toothed wheels (12, 13) which are connected to each other via a toothed segment (14).

9. The device according to claim 6, characterized in that, the oscillation generator for generating a vibration of the stationary counter-jaw (3, 21) and/or of the guide segment (6, 34) of the test specimen (7) is a vibrator (24, 27) that has a plunger (30) that engages stationary counter-jaw (3, 21) and/or the guide segment (6, 34).

10. The device according to claim 9, characterized in that, the vibrator (24, 27) has an electromagnet (28) as well as a pull-back spring (29).

11. The device according to claim 7, characterized in that, above the stationary counter-jaw (3, 21), there is a video camera (35) for monitoring the docking of the test specimen (7) at the stationary counter jaw (3, 21), said camera generating an electric signal that serves to influence the electric motor (15).

12. A device for aligning and moving a test specimen (7) such as, for instance, tablets, pills, lozenges or tabs, which are cambered or rounded on at least one of their main surfaces and are thus able to execute rocking oscillations starting from a resting position, in order to carry out another process step such as a hardness test or a pushing over procedure, involving the test specimen (7), having a movable pushing jaw (2) for moving the test specimen (7) an a guide segment (6, 34) so as to initiate the further process step involving the test specimen (7), characterized in that, the pushing jaw (2), with a continuous interruption of its advancing movement, can be moved back and forth along small advancing and retreating distances relative to its total advancing distance, but all in all, while each time carrying along the test specimen (7) on the guide segment (6, 34) by the small advancing distance and releasing the test specimen by retreating, can be moved until the test specimen (7) has reached the desired place (3, 21), or in that the guide segment (6, 34) can be made to oscillate around a resting position during the advancing movement of the movable pushing jaw (2) by means of an oscillation generator (24, 27), said oscillations acting on the test specimen (7) so that the test specimen (7) is also able to execute a rocking and/or vibrating oscillation during the advancing movement of the movable pressing jaw (2).

* * * * *

UNITED STATES PATENT AND TRADEMARK OFFICE
CERTIFICATE OF CORRECTION

PATENT NO. : 7,364,103 B2
APPLICATION NO. : 10/531559
DATED : April 29, 2008
INVENTOR(S) : Norbert Kraemer It is certified that error appears in the above-identified patent and that said Letters Patent is hereby corrected as shown below:

On the title page add

(73) Assignee: Thilo KRAEMER, Darmstadt (DE)

Signed and Sealed this

Thirteenth Day of January, 2009

JON W. DUDAS
*Director of the United States Patent and Trademark Office*